United States Patent [19]

Horvath

[11] Patent Number: 5,127,420
[45] Date of Patent: Jul. 7, 1992

[54] APPARATUS AND METHOD FOR FITTING A PROSTHESIS SOCKET

[75] Inventor: Eduard Horvath, Vienna, Austria

[73] Assignee: Otto Bock Orthopadische Industrie Besitz- und Verwaltungs-KG, Duderstadt, Fed. Rep. of Germany

[21] Appl. No.: 663,146

[22] Filed: Feb. 28, 1991

[30] Foreign Application Priority Data

Feb. 28, 1990 [AT] Austria .................................. 476/90

[51] Int. Cl.$^5$ .......................................... A61B 5/103
[52] U.S. Cl. .................................................. 128/782
[58] Field of Search ............. 128/774, 779, 782, 80 F, 128/80 DB; 623/27, 28, 33, 36, 38, 66

[56] References Cited

U.S. PATENT DOCUMENTS

| | | | |
|---|---|---|---|
| 4,062,355 | 12/1977 | Kaye | 128/779 |
| 4,416,269 | 11/1983 | Enomoto et al. | 128/41 |
| 4,667,685 | 5/1987 | Fine | 128/782 |
| 4,819,660 | 4/1989 | Smith | 128/774 |
| 4,923,476 | 5/1990 | Cooper et al. | 623/38 |
| 5,014,719 | 5/1991 | McLeod | 128/774 |

FOREIGN PATENT DOCUMENTS

| | | |
|---|---|---|
| 867427 | 10/1949 | Fed. Rep. of Germany . |
| 1291855 | 6/1963 | Fed. Rep. of Germany . |
| 2027212 | 11/1971 | Fed. Rep. of Germany . |
| 8603970 | 1/1988 | Fed. Rep. of Germany . |
| 2121688 | 1/1984 | United Kingdom . |
| 2188846 | 10/1987 | United Kingdom . |
| WO88/04536 | 6/1988 | World Int. Prop. O. . |

*Primary Examiner*—Max Hindenburg
*Assistant Examiner*—Guy V. Tucker
*Attorney, Agent, or Firm*—Herbert Dubno

[57] ABSTRACT

The service characteristics of a prosthesis shaft for a limb stump projecting from a pivotal articulation of a patient are determined by first fitting the shaft while engaged over the limb stump into a holder pivotal about a holder axis and then aligning the holder axis so that it generally traverses the articulation. The shaft and holder are then moved by the stump pivotally about the axis to establish extreme positions of the holder that cause discomfort to the patient. Movement within the extreme positions is established as an actual-value range and compared with a desired-value range. Then the fit of the shaft on the stump is adjusted and the first three steps are repeated until the actual-value range generally corresponds to the desired-value range. Normally the holder is pivotal about two generally perpendicular and coplanar holder axes and the intersection of the axes being set generally at the articulation.

13 Claims, 4 Drawing Sheets

APPARATUS AND METHOD FOR FITTING A PROSTHESIS SOCKET

FIELD OF THE INVENTION

The present invention relates to a method of and apparatus for testing the fit of a prosthesis socket. More particularly this invention concerns a system for determining the useful movement range of a prosthesis socket on a limb stump for adjusting the fit of the socket.

BACKGROUND OF THE INVENTION

In the construction of prostheses, in particular false legs, there are a variety of techniques. The primary considerations are of course both technical and cosmetic. Ahead of every aspect, however, the main consideration is service characteristics, namely whether the device is comfortable and functions, since if it does not satisfy both these requirements the patient will not use the prosthesis.

Typically the construction of false limbs is the domain of specialists whose decisions are in part based on intuition and in part on experience. Even when computer technology is applied to the problem of artificial-limb design, it is normally left to the designer to make up the most important part, namely the socalled socket shaft that fits over the patient's stump. This part must fit so that on the one hand it can support the load of the limb and/or of the patient, but also so that when the stump is moved through the full normal range of movement, it remains comfortable. Typically the fitting of the socket entails a lengthy process where the patient's subjective impressions of successive adjustments to the fit are followed, along with direct observations by the maker of the device.

At best such procedures are haphazard. Successive adjustments of socket fit are frequently off the mark and sometimes even make the device less comfortable or reduce the useful range of the limb.

OBJECTS OF THE INVENTION

It is therefore an object of the present invention to provide an improved method of and apparatus for determining the service characteristics for a prosthesis shaft for a limb stump.

Another object is the provision of such an improved method of and apparatus for determining the service characteristics for a prosthesis shaft for a limb stump which overcomes the above-given disadvantages, that is which allows one to accurately and scientifically determine the relationship between the fit of the socket and the range of movement that it will provide with a given fit.

A further object is to provide an improved system that allows a socket to be perfectly fit to a patient while giving him a near perfect or ideal range of movement of the limb to eventually be built on the socket.

SUMMARY OF THE INVENTION

According to the invention the limb stump is inserted into the prosthesis shaft which has a socket accommodating the stump and which is adapted to receive the prosthetic mechanism. The prosthesis shaft, receiving the limb stump, is carried by a support device adjusted to be swingable about an axis, preferably two mutually intersecting and especially mutually perpendicular axes, wherein the axis or the intersection point of the axes correspond in location to a center region of the natural joint of the limb or the thrust point thereof. Thereafter the prosthesis shaft is moved by means of the stump and the limits of mobility of the shaft which do not result in pain caused by the pressure of the socket of the shaft against the stump are determined. These limits can be obtained as coordinate values of a boundary of an actual value mobility range which is compared with standardized setpoint values of acceptable ranges to determine deviations between the actual and setpoint values. Then the shaft socket is altered so as to reduce these deviations between the actual values and setpoint values of shaft mobility.

Thus, a method of determining the service characteristics of a prosthesis shaft for a limb stump projecting from a pivotal articulation of a patient according to the invention comprises first fitting the shaft while engaged over the limb stump into a holder pivotal about a holder axis and then aligning the holder axis so that it generally traverses the articulation. The shaft and holder are then moved by the stump pivotally about the axis to establish extreme positions of the holder that cause discomfort to the patient. Movement within the extreme positions is established as an actual-value range and compared with a desired-value range. Then the fit of the shaft on the stump is adjusted and the first three steps of fitting, aligning, and testing by moving are repeated until the actual-value range generally corresponds to the desired-value range. Normally according to the invention the holder is pivotal about two generally perpendicular and coplanar holder axes and the intersection of the axes being set generally at the articulation.

With this procedure, therefore, the range of movement of the socket is tested and all the patient need comment on is how the socket feels in any given position. Thus the patient moves, for example, his upper-leg stump forward until it can go no further or until it is impeded by the socket, and this position is marked. Then this is repeated for backward, side-to-side, and all other movements for the stump to ascertain exactly what types of motion are inhibited by the socket. Once this is done the maker can shave material off or add material to the socket in the appropriate places in a scientific manner, without affecting portions of the socket that are giving no problems. There is no general question of comfort of feel, instead the patient need merely respond at a given point in the movement range to whether he or she is being impeded or hurt by the socket. Of course if the patient is able to move to a given desired-value position, this aspect of the socket is not in need of adjustment. The desired-value range itself can be empirically derived and typically comprises a region on the floor where the foot of the patient would normally land during walking.

In order to complete the prostheses the mechanical elements of the prostheses are then constructed on the shaft according to the data derived according to the method of this invention, whereby anomalies such as for example a bow-legged or knock-kneed condition can be taken into account. The prosthesis can be provided with corrections of the requisite cosmetic shape, optimizing both appearance and function.

By means of a known auxiliary device (i.e. a digitizer), I can generate digitalized data providing a computer-true description of the stump bed or shaft socket, preferably in an orientation of the shaft in which the actual-value curve is determined.

The limits of movement are therefore that angle to which the shaft can be moved without pain for the patient. Use of the method allows the patient to input to the measuring system, without influencing or observing the results, his pain feelings so that the limits of the prostheses are established in the relevant movement directions with greater scientific precision.

The apparatus for carrying out this method comprises a base, normally one on which the patient stands and that is provided with a support column carrying the pivotal holder. Sensors are provided for detecting pivoting of the holder about its axes and the position of the holder when pivoted relative to the base and for generating outputs corresponding thereto and some means is provided for registering extreme positions when the holder causes discomfort to the patient, typically in the form of a handle or grip the patient moves in these extreme positions. A computer-type controller is connected to the sensor means and to the means for registering for establishing movement within the extreme positions as an actual-value range and comparing it with a desired-value range in accordance with a preset program. Then of course the fit of the shaft on the stump can be adjusted until the actual-value range generally corresponds to the desired-value range.

According to a feature of this invention the holder includes an inner part pivotal about one of the axes on the base and an outer part pivotal about the other of the axes on the inner part. The holder further includes a seat snugly engageable around the shaft and the seat can be shifted and positioned on the outer part, typically by means of a pair of transversely oriented cross slides. Furthermore the seat is pivotal on the inner part about a third axis generally perpendicular to the plane of the first two axes at the intersection thereof.

At least one sensor is provided on at least one of the parts for producing an output corresponding to the rotation of the respective part about the respective axis so that the exact angular position at which the patient starts to experience discomfort can be accurately determined. Furthermore sensors can include means for detecting the torque applied by the patient to the holder in the extreme positions. Thus the controller can know how much pressure the patient is exerting on shaft at any of its critical extreme positions. In this manner it is possible to determine just how much force the patient must exert in a particular position to experience discomfort or pain, thereby further delimiting the effective range of a given shaft.

According to a further feature of this invention a brake, typically a brake (or brake generator) and/or a motor is connected to at least one of the parts for inhibiting and/or effecting rotation thereof about the respective axis. This makes it possible to accurately imitate the forces which apply in actual use of the prosthetic limb.

The motor at the relatively rotatable parts of an axis or the motors between the relatively rotatable parts at the respective axes permit the requisite movements unassisted by the patient and the brake or brakes can be used to establish the torques required at each axis for movement in the respective direction or to hinder such movement. Means can be additionally provided for imparting shock loads to the shaft.

Further according to this invention the base of the apparatus is provided with means for weighing the patient and the support is equipped with means for measuring the amount of force the patient bears down on the support with. Thus the amount of weight being applied to the shaft, which should periodically be the patient's entire weight, can be monitored. In order to, for instance, simulate the shock of walking, a device is provided for administering shocks to the support. This device delivers upward blows to the support so that they are transmitted therethrough to the shaft. Such shocks can correspond to the shocks transmitted to the leg when the shoe strikes the ground.

BRIEF DESCRIPTION OF THE DRAWING

The above and other objects, features, and advantages will become more readily apparent from the following, reference being made to the accompanying drawing in which.

SPECIFIC DESCRIPTION

Figure 1:
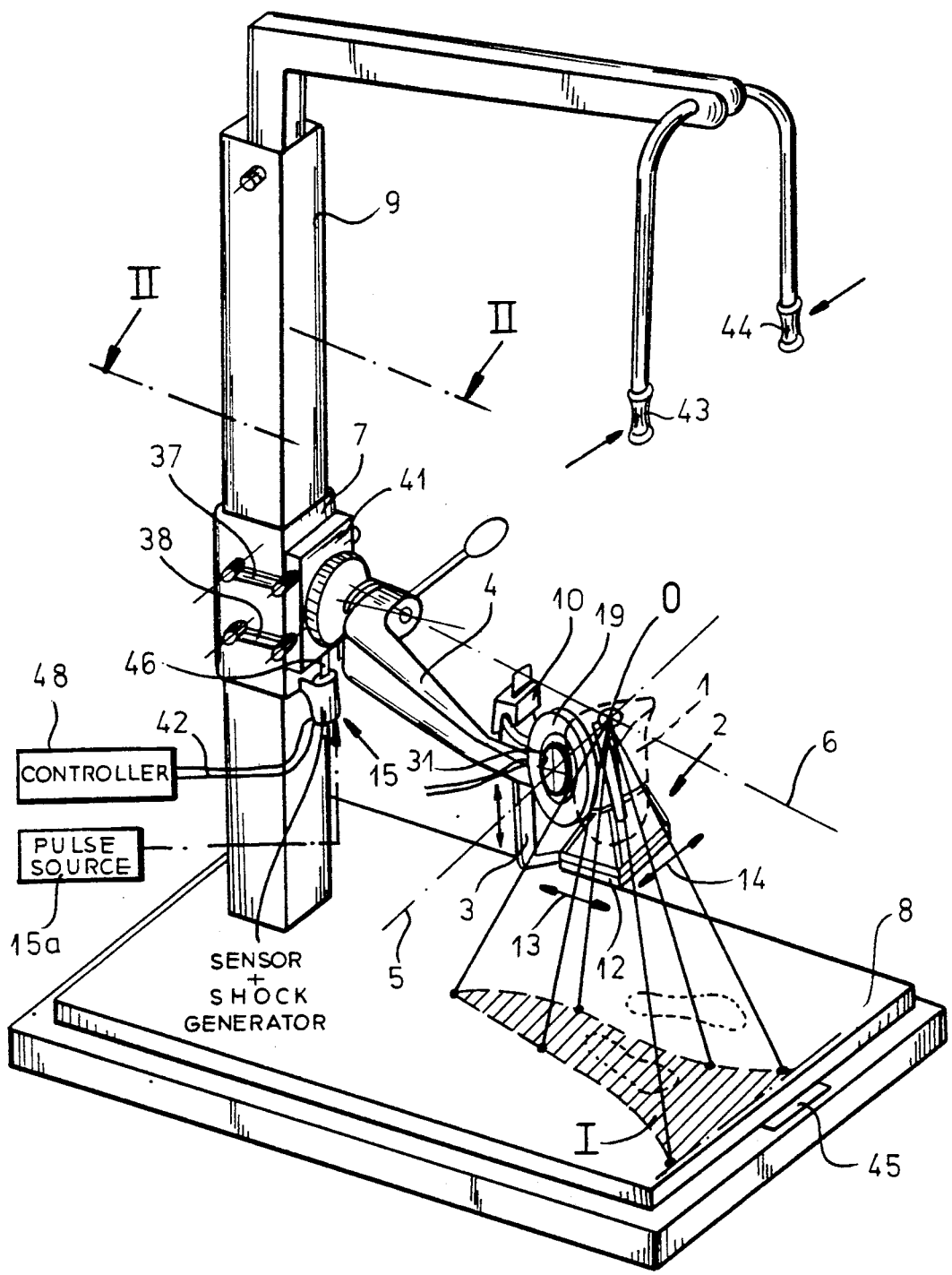
FIG. 1 is a partly diagrammatic isometric view of the apparatus for carrying out the method of the invention.

As seen in the drawing a socket 1, here intended to receive an upper-leg stump, is secured in a holder 2 itself carried on an outer L-shaped support arm 3 suspended from a curved bracket 16 carried on a main support arm 4. The bracket 16 and arm 3 can pivot about a normally horizontal axis 5 (forming one holder axis) relative to the arm 4 and this arm 4 can in turn pivot about a normally horizontal axis 6 perpendicular to the axis 5 on a support slide 7. A base plate 8 has an upright column 9 to which the slide 7 is securable at any of a multiplicity of vertically offset positions.

Figure 3:
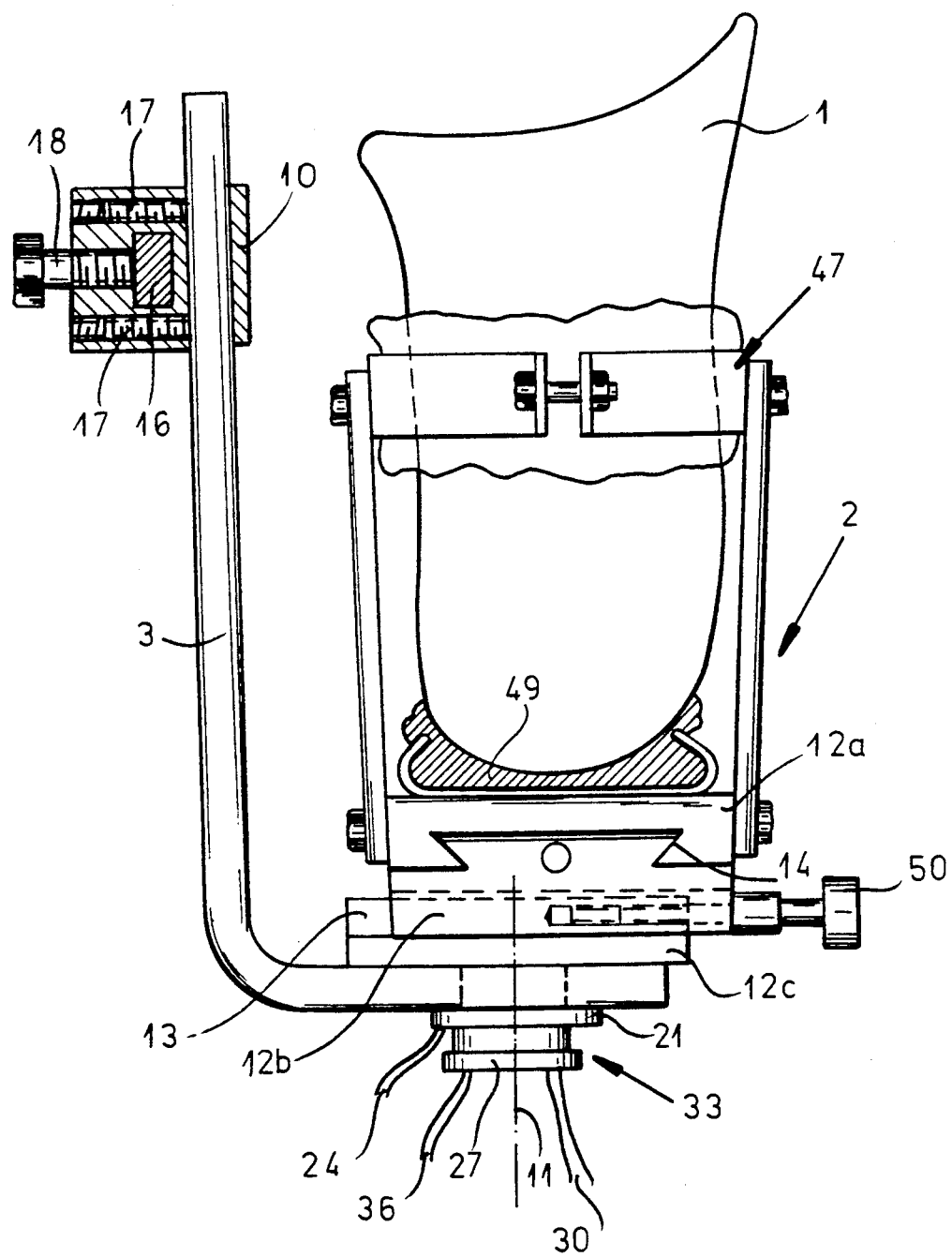
FIG. 3 is a large-scale vertical section showing the socket holder of this invention.

The holder arm 3 is connected as seen in FIG. 3 to a slide block 10 in which the arm 3 can move vertically and can be locked in any position by screws 17. The block 10 can also slide horizontally along the bracket 16 and be locked in position by another such screw 18. The holder 2 has a collar 47 that can be tightened around the socket shaft 1 and a seat 49 into which the end of the socket 1 is seated. This holder 2 is pivotal about a vertical axis 11 (forming another holder axis) on the support arm 3 but is connected thereto via two mutually perpendicular cross slides 13 and 14 interconnecting an upper plate 12a having the seat 49, and intermediate plate 12b connected via the side-to-side cross slide 14 to the plate 12a, and a lower plate 12c connected the front-to-back cross slide 13 to the intermediate plate 12b and itself pivotal on the lower end of the arm 3 about the axis 11. Respective adjustment screws such as shown at 50 for the slide 13 are provided for relatively setting the positions of the cross slides 13 and 14.

Respective sensors 19, 20, and 21 are provided for determining the angular positions of the arm 4 relative to the axis 6 and the holder 2 relative to the axes 5 and 11. The outputs from these sensors 19, 20, and 21 are fed via respective lines 22, 23, and 24 to a controller indicated schematically at 48 in FIG. 1. In addition a motor and/or brake 25, 26, and 27 is associated with each of these sensors 19, 20, and 21 for effecting or retarding rotation about the respective axis 5, 6, and 11. These devices 25, 26, and 27 are in turn associated with torque sensors 31, 32, and 33 connected via lines 34, 35, and 36 to the controller 48 to supply same with outputs indicating the force applied relative to the respective axes.

The base plate 8 is constructed as a scale with a weight sensor 45 connected to the controller 48, and pendant handles 43 and 44 are provided that hang from the top of the column above and to either side of the support 2. These handles 43 and 44 are also constituted as sensors which can be squeezed by the user to furnish an output to the controller 48 as described below.

The slide 7 is connected via links 37, 38, 39, and 40 to a support 41 on which the pivot for the arm 4 about the axis 6 is carried. The links 37 through 40 form parallelogrammatic linkages which permit limited vertical movement of the support block 41 relative to the stationary slide 7. A combined sensor and shock generator 15 is provided on the slide 7 to detect the vertical position of the block 41 relative to the slide 7 and the weight being applied downward to the block 41 and to furnish an output corresponding thereto via a line 42 to the controller 48. The sensor 15 also functions as a shock generator for transmitting shocks to the socket shaft 1 via the arm 4. The shock generator is thus fixed on the column 9 or on the slide 7 and is supplied with electrical energy from a source 15a in order to transmit shocks via the block 41 along the axis 6 by means of a vertically displaceable pin 46.

Figure 2:
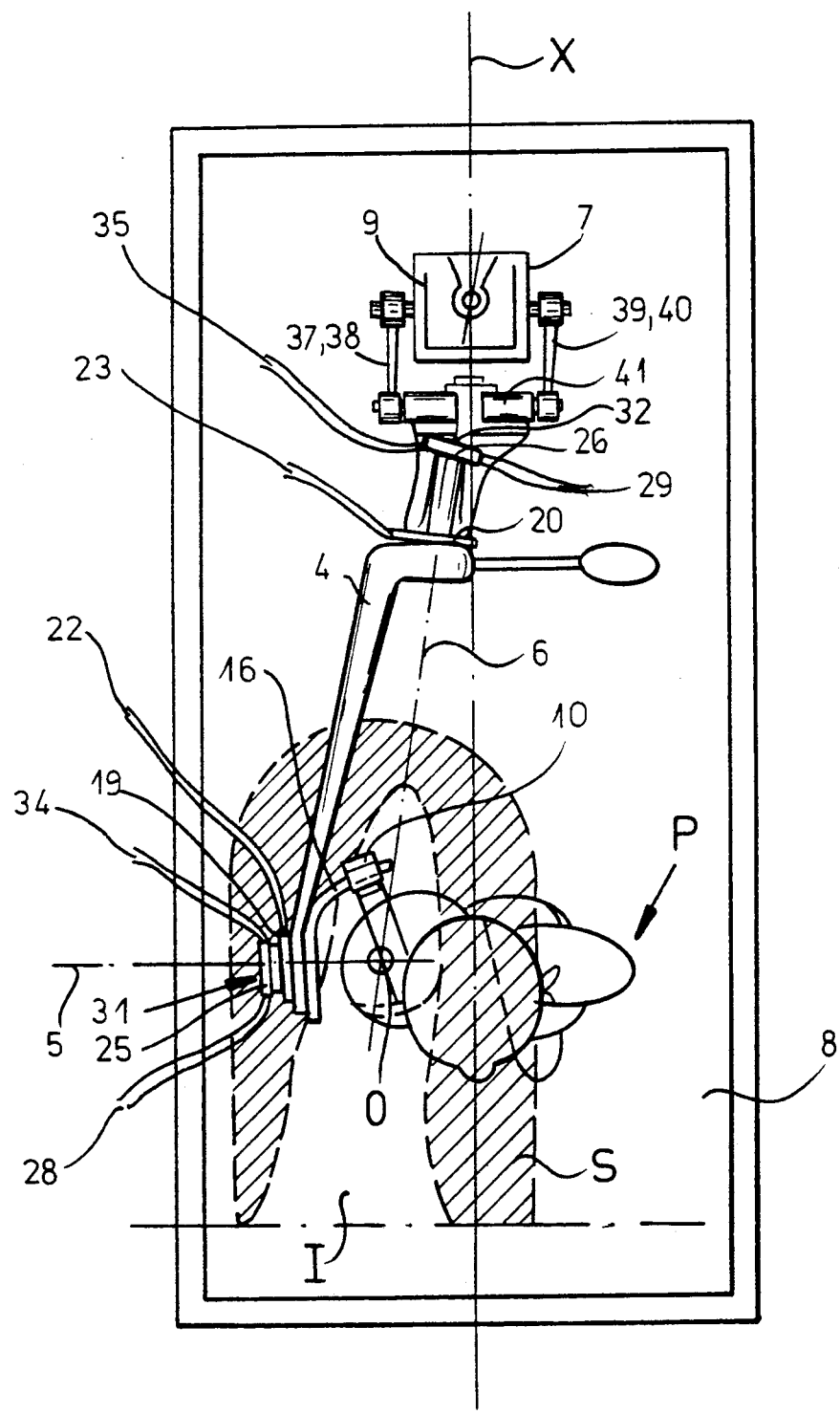
FIG. 2 is a top view partly in section taken along line II—II of FIG. 1.
Figure 4:
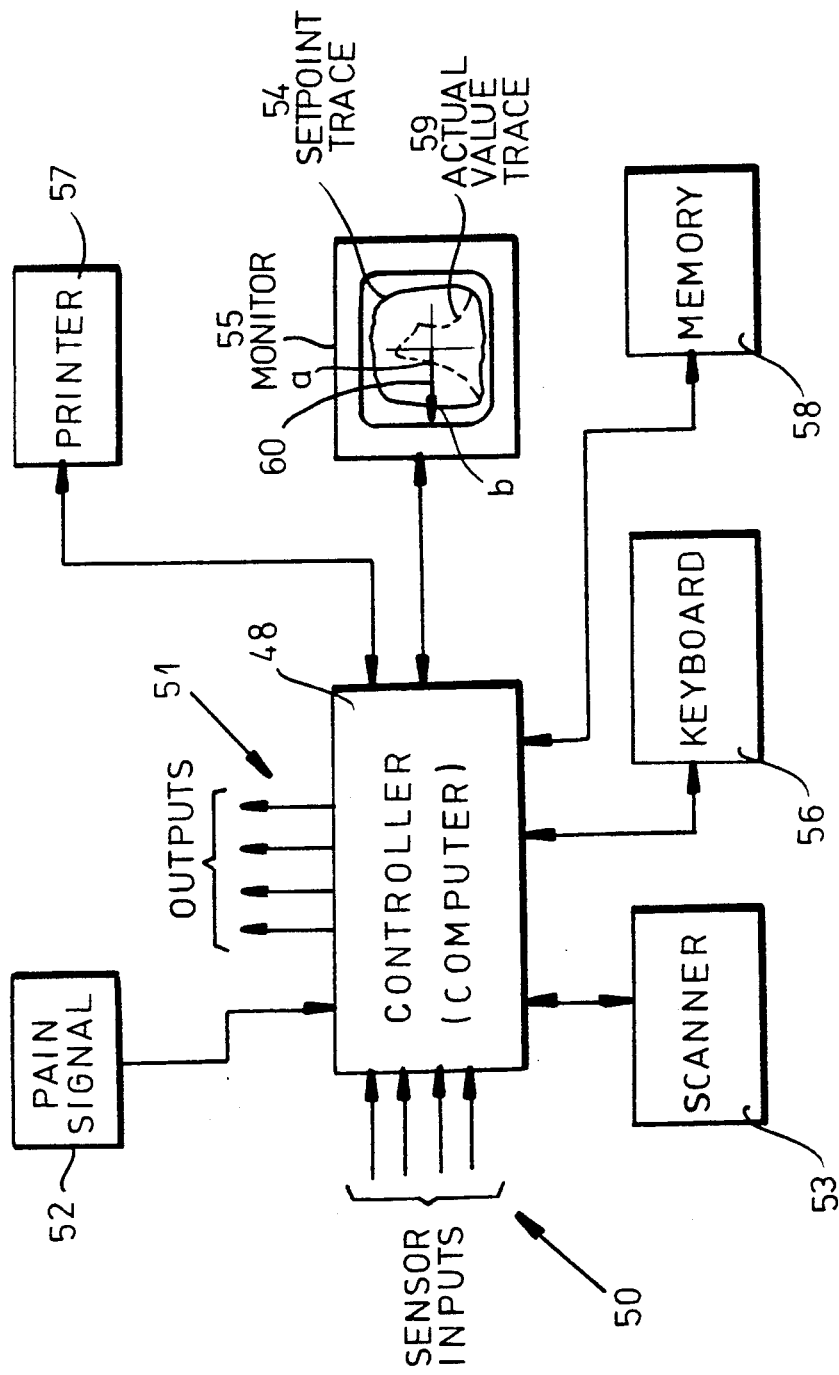
FIG. 4 is a block diagram of a circuit used with the apparatus of FIGS. 1-3.

In FIG. 4 I have shown, in block diagram form a circuit which can be used with the system of FIGS. 1-3. The controller or computer 48 has inputs 50 representing the sensor outputs of the apparatus and outputs 51 to the motors for generating torque about the axes and to the shock-pulse generator 15. An additional input 52 represents the pain signal transmitted by the patient when experiencing pain.

The computer 48 is connected with a scanner 53 by means of which a setpoint movement trace 54, visible on a monitor display 55, can be inputted. Data as to the setpoint latitudes of movement in any direction can also be inputted by a keyboard 56 and a printer 57 can display data obtained by the apparatus and corrections of the socket which may be indicated. The computer is associated with a memory 58 which can store empirically derived data equating a particular difference in coordinates of a setpoint and actual value with a particular correction in the shape of the stump socket. Thus if, the actual value trace 59 is obtained, for a specific moment vector 60, the actual value point a can have the coordinates (n, $\pi$) whereas the corresponding setpoint b would have the coordinates (n+e, $\pi$) in polar coordinates. The difference e is determined by the computer and the printout would indicate that a correction e would require modification of the socket at a particular location and to a given degree to increase mobility in that direction. After reshaping of the socket the measurement can be repeated as will be described below.

In use a patient P stands with his or her good leg on the plate 8 facing forward along a vertical symmetry plane X bisecting the column 9 and perpendicular to the axis 5. The patient's stump is fitted into his or her own socket 1 which is clamped in the holder 2 that is adjusted via the screws 17, 18, and 50 until it is in a comfortable and natural position with the axis 6 extending through the patient's hip joint. The patient P applies weight to the socket 1 and can in fact support his or her entire weight thereon, which fact can readily be determined by comparing the weight readout of the sensors 15 and 45 that are connected to the controller 48.

Once thus in place the patient P moves his stump and the socket 1 from front to back and from side to side, all of which movements are of course pivoted on a point O lying at the intersection of the axes 5 and 6 in the patient's hip joint. Whenever the patient P experiences discomfort he or she pushes the handles 43 apart to signal this to the controller 48.

Thus the controller 48 will be able to determine the position at which movement in any direction becomes uncomfortable, and the force being exerted by the patient P at this position on the shaft 1. The controller 48 is therefore able to establish an imaginary projection or field I (FIG. 2) corresponding to the actual comfortable range of movement for the patient, and compare it to another such field S that represents the desired maximum movement range. When the actual-value field I is short of the desired-value field S this is an indication that the socket 1 is binding the patient and inhibiting his or her movement. Thus the socket 1 can be worked on, either having material removed or added as appropriate, and the test can be rerun to determine if the correction actually does improve the range of movement. To start with, the actual-value field I is normally centered in the desired-value field S by adjustment of the screws 50 and of course the block 10 is adjusted to set the point O right in the patient's hip articulation. This starting-up adjustment also helps later setting of the position of the socket 1 in the leg prosthesis to be built.

Clearly this arrangement can also be adapted for use with other limbs. In the case, for instance, of use with a lower-arm stump, the center O is set at the elbow and of course the axes 5 and 6 are set to correspond to normal arm movements.

I claim:
1. A method of determining the service characteristics of a prosthesis shaft for a limb stump projecting from a pivotal articulation of a patient, the method comprising the steps of:
   a) fitting the shaft while engaged over the limb stump into a holder pivotal about a holder axis;
   b) aligning the holder axis so that it generally traverses the articulation;
   c) moving the shaft and holder by means of the stump pivotally about the axis and establishing extreme positions of the holder that cause discomfort to the patient;
   d) establishing movement within the extreme positions as an actual-value range and comparing it with a desired-value range; and
   e) adjusting the fit of the shaft on the stump and then repeating step a) through c) until the actual-value range generally corresponds to the desired-value range.

2. The method defined in claim 1 wherein the holder is pivotal about two generally perpendicular and coplanar holder axes, the intersection of the axes being set in step b) generally at the articulation.

3. An apparatus for determining the service characteristics of a prosthesis shaft for a limb stump projecting from a pivotal articulation of a patient, the apparatus comprising:
   a base;
   a holder provided with means for snugly holding the prosthesis shaft while engaged o the stump of the patient;
   means supporting the holder on the base for pivoting thereon about two generally perpendicular and holder axes;
   means for aligning an intersection of the holder axes so that the holder axes generally transverse the articulation of the patient whose limb stump is fitted to the shaft engaged in the holder;

sensor means for detecting pivoting of the holder about said holder axes and the position of the holder when pivoted relative to the base;

means for registering extreme positions when the holder causes discomfort to the patient; and control means connected to the sensor means and to the means for registering for establishing movement within the extreme positions as an actual-value range and comparing it with a desired-value range, whereby the fit of the shaft on the stump can be adjusted until the actual-value range generally corresponds to the desired-value range.

4. The apparatus defined in claim 3 wherein the holder includes an inner part pivotal on the base about one of said holder axes and an outer part pivotal on the inner part about the other of the holder axes.

5. The apparatus defined in claim 4 wherein the holder includes a socket snugly engageable around the shaft and the means for aligning includes means for shifting and positioning the socket on the outer part.

6. The apparatus defined in claim 5 wherein the seat is pivotal on the inner part about a third axis generally perpendicular to the plane of said holder axes at the intersection thereof.

7. The apparatus defined in claim 5 wherein the means for shifting includes a pair of transversely oriented cross slides.

8. The apparatus defined in claim 4 wherein the sensor means includes at least one sensor on at least one of the parts for producing an output corresponding to the rotation of the respective part about the respective axis.

9. The apparatus defined in claim 4 wherein the sensor means includes means for detecting the torque applied by the patient to the holder in the extreme positions, the torque-detecting means being connected to the control means.

10. The apparatus defined in claim 4, further comprising brake means connected to at least one of the parts for inhibiting rotation thereof about the respective axis.

11. The apparatus defined in claim 4, further comprising motor means connected to at least one of the parts for rotating same about the respective axis.

12. The apparatus defined in claim 4 wherein the base is equipped with means for weighing the patient and the support is equipped with means for measuring an amount of force with which the patient bears down on the support.

13. The apparatus defined in claim 4, further comprising means for administering shocks to the support.

* * * * *